United States Patent
Bazin et al.

(10) Patent No.: US 7,226,760 B2
(45) Date of Patent: Jun. 5, 2007

(54) METHOD FOR PREPARING A FLUID ABSORBER

(75) Inventors: Hélène G. Bazin, Cincinnati, OH (US); Frank W. Barresi, Coralville, IA (US)

(73) Assignee: Grain Processing Corporation, Muscatine, IA (US)

(*) Notice: Subject to any disclaimer, the term of this patent is extended or adjusted under 35 U.S.C. 154(b) by 577 days.

(21) Appl. No.: 10/459,292

(22) Filed: Jun. 11, 2003

(65) Prior Publication Data

US 2003/0202996 A1    Oct. 30, 2003

Related U.S. Application Data

(62) Division of application No. 09/971,239, filed on Oct. 4, 2001, now Pat. No. 6,946,148.

(60) Provisional application No. 60/237,918, filed on Oct. 4, 2000.

(51) Int. Cl.
*C12P 19/14* (2006.01)
*C12P 19/22* (2006.01)
*C12P 19/20* (2006.01)
*C12P 12/16* (2006.01)

(52) U.S. Cl. .................... 435/99; 435/95; 435/96; 435/98

(58) Field of Classification Search ............ 435/99, 435/101, 95, 96, 98
See application file for complete search history.

(56) References Cited

U.S. PATENT DOCUMENTS

| | | |
|---|---|---|
| 2,583,451 A | 1/1952 | Wallerstein et al. |
| 3,922,198 A | 11/1975 | Kuske et al. |
| 3,922,199 A | 11/1975 | Hebeda et al. |
| 3,992,196 A | 11/1976 | Ando |
| 3,992,201 A | 11/1976 | Koo et al. |
| 4,113,509 A | 9/1978 | Leach et al. |
| 4,551,177 A | 11/1985 | Trubiano et al. |
| 4,568,539 A | 2/1986 | Ashton et al. |
| 4,603,110 A | 7/1986 | Morehouse et al. |
| 4,612,284 A | 9/1986 | Pickens et al. |
| 4,618,579 A | 10/1986 | Dwiggins et al. |
| 4,985,082 A | 1/1991 | Whistler |
| 5,011,696 A | 4/1991 | Haas et al. |
| 5,415,861 A * | 5/1995 | Duffy et al. ............... 424/401 |
| 5,445,950 A | 8/1995 | Kobayashi et al. |
| 5,886,124 A | 3/1999 | Kightlinger et al. |
| 5,904,941 A | 5/1999 | Xu et al. |
| 5,919,486 A | 7/1999 | Ishii et al. |
| 5,935,826 A | 8/1999 | Blue et al. |
| 6,054,302 A * | 4/2000 | Shi et al. ..................... 435/95 |
| 6,608,017 B1 * | 8/2003 | Dihora et al. ............... 510/349 |

FOREIGN PATENT DOCUMENTS

| | | |
|---|---|---|
| EP | 0 182 296 A2 | 5/1986 |
| JP | 05112469 A2 | 5/1993 |
| JP | 6122612 A2 | 5/1994 |
| JP | 8277230 A2 | 10/1996 |
| JP | 10182701 A2 | 7/1998 |
| JP | 11334199 A2 | 12/1999 |
| JP | 2000/109882 | 4/2000 |
| WO | WO 96/10586 | 4/1996 |

OTHER PUBLICATIONS

Sathe et al. "Isolation, partial characterization and modification of the great Northern bean (*Paseolus vulgaris* L.) starch" J. Food Sci. (1981) 46: 617-621.*
Belshaw, Nigel J. and Gary Williamson, Interaction of B-cyclodextrin with the granular starch-binding domain of glucoamylase. Biochimica er Biophysica Act 1078 (1991) 117-120.
Neimann, Claudia and Roy Whistler, Effect of Acid Hydrolysis and Ball Milling on Porous Corn Starch, starch/starke, 44(11) (1992) 409-414.
Reichert, E.T., Publication of the Carnegie Institution at Washington, 173, Part 1 (1913) 113-154 and 165 181.
Svensson, Birte, Kjeld Larsen and Alf Gunnarsson, Characterization of a Glucoamylase G2 from *Aspergillus niger*, 154 (1986) 497-502.
Walker, Gwen J. and Pamela M. Hope, The action of some x-Amylases on Starch Granules, J. Biochem, 86 (1963) 452-462.

* cited by examiner

*Primary Examiner*—L. Blaine Lankford
*Assistant Examiner*—Susan Hanley
(74) *Attorney, Agent, or Firm*—Banner & Witcoff, Ltd.

(57) ABSTRACT

Disclosed are a fluid absorber, a method for preparing a fluid absorber, and a method for absorbing fluid from the skin. The disclosed method for preparing a fluid absorber generally comprises the steps of selecting a starch and an enzyme for hydrolysis of the starch, determining a fluid absorption optimum hydrolysis level for the starch, and ezymatically hydrolyzing the starch to approximately the optimum level thus determined. The starch alternatively may be hydrolyzed with acid hydrolysis without the use of an enzyme catalyst. The disclosed method for absorbing fluid from the skin includes the step of applying a fluid absorbing effective amount of a fluid absorber thus prepared. Absorption properties of the fluid absorber of the invention are comparable to or exceed those of commercially available skin fluid absorbers, such as talc and unmodified corn starch.

8 Claims, 2 Drawing Sheets

METHOD FOR PREPARING A FLUID ABSORBER

RELATED APPLICATION

This application is a divisional of U.S. application Ser. No. 09/971,239, filed Oct. 04, 2001, now U.S. Pat. No. 6,946,148, which claims benefit of prior provisional U.S. application No. 60/237,918, filed Oct. 04, 2000.

TECHNICAL FIELD OF THE INVENTION

The invention relates to a method for absorbing fluid from the skin, and towards a method for preparing a fluid absorber that is suitable for absorbing fluid from the skin. The invention further provides a fluid absorber which functions as a carrier for other products, in particular oleogenous products such as certain flavorings, and provides a method for absorbing such fluid, and a product carried by such a fluid absorber. The fluid absorber used in conjunction with the invention comprises granular starch that has been partially hydrolyzed, preferably via enzymatic hydrolysis.

BACKGROUND OF THE INVENTION

Enzymes capable of hydrolyzing granular starch at temperatures below the starch gelatinization temperature are known in the art. For instance, it has long been known that alpha-amylases can hydrolyze granular starch, as disclosed in, for instance, Richert et al., *Publication of the Carnegie Institution at Washington*, No. 173, Part 1 (1913). More recently, other enzymes, such as glucoamylase enzymes, have also been found to hydrolyze granular starch below the starch gelatization temperature. It is believed that the presence of a starch-binding domain is essential for an enzyme to hydrolyze granular starch; numerous enzymes having such domains are known, as disclosed, for instance, in Walker, G. J. et al. *Biochemical Journal*, 86:452 (1963); Belshaw, N.J. et al., *Biochim. Biophys. Acta*, 1078:1117-20 (1991), and Svensson, B. et al., *Eur. J. Biochem.*, 154:497-502 (1986). As is well known in the art, the term "enzyme hydrolysis" refers to enzyme-catalyzed hydrolysis, and thus enzymes such as alpha-amylase can be regarded as "hydrolyzing" starch via a catalytic hydrolytic action.

As is also known in the art, when a granular starch is treated with an alpha amylase or a glucoamylase, the granular structure of the starch degrades, leaving behind a porous starch granule upon partial hydrolysis of the starch, or, if the enzymatic hydrolysis is allowed to continue, yielding a starch hydrolyzate or ultimately glucose or another lower order sugar. It is also recognized that the enzymatic attack on starch granules takes place by exo-corrosion in which the enzyme either erodes the entire surface of the granule or digests a channel from points on the surface towards the center of the granule. In the latter mode of attack, once the center is reached, the enzymatic attack proceeds outwardly from the center over a broader front. The internal structure of a porous starch granule that has been so modified is open and cavernous and can exhibit either a terraced or a step-shaped appearance.

When a glucoamylase enzyme is allowed to completely hydrolyze a starch granule, the resulting product typically is glucose. U.S. Pat. Nos. 2,583,451; 3,922,198; 3,922,199; 4,612,284; and 4;618,579 disclose processes for converting granular starch to glucose by treating of the starch with glucoamylase or a mixture of glucoamylase with alpha-amylase. Other reaction products are possible; for instance, U.S. Pat. No. 3,922,201 discloses a process for the preparation of levulose-containing compositions from granular starch by treating the starch with alpha-amylase, glucoamylase, and glucose isomerase.

The prior art also has described the enzymatic hydrolysis of starch below the gelatinization temperature to produce starch hydrolyzes other than glucose. For instance, U.S. Pat. No. 3,922,196 discloses a process for converting granular starch to a starch hydrolyzate having a DE (dextrose equivalent) between 40 and 55 and including a high percentage of disaccharides and trisaccharides. The process disclosed in this patent employs alpha-amylase, glucoamylase, beta-amylase and isoamylase. Another document, U.S. Pat. No. 4,113,509, discloses an enzymatically produced high maltose-maltotriose starch hydrolyzate having a DE of 40 to 55. This patent discloses a process in which alpha-amylase, alone or with a saccharifying enzyme such as glucoamylase or beta-amylase, is used to hydrolyze the starch. Methods for the production of other malto-oligosaccharides such as maltose and maltotetraose by treatment of starch with specific alpha-amylases have also been employed on an industrial scale.

The prior art also has provided applications for porous starches that are obtained by partial enzymatic digestion of the granular starch. For instance, U.S. Pat. No. 4,985,082 discloses a starch matrix material comprising granular starch that is partially hydrolyzed with an alpha-amylase and/or a glucoamylase and treated chemically to modify the structural integrity and surface characteristics of the starch. The disclosed starches are said to be useful as adjuvants for antiperspirants and as bulking agents for foods and drinks. U.S. Pat. No. 4,551,177 discloses a compressible starch said to be useful as a binder for a tablet or capsule and which is said to be prepared by treating granular starch with an acid and/or with an alpha-amylase enzyme at a temperature below the gelatinization temperature of the starch. Yet another document, U.S. Pat. No. 5,445,950, discloses a method of using alpha amylase to prepare slightly decomposed starch granules having low viscosity. The starch granules are said to be useful as a raw material in the starch and sugar industry. U.S. Pat. No. 5,904,941 discloses a viscosifier that comprises an enzymatically hydrolyzed, ungelatinized granular starch with a dextrose equivalent of from about 5 to 60. Still another document, U.S. Pat. No. 5,935,826, discloses a modified starch prepared by the glucoamylase hydrolysis of a starch derivative that contains a hydrophobic group or both a hydrophobic and a hydrophilic group. The starches are said to be characterized by having a DE from 20 to 80, and are said to be useful as emulsifiers or an encapsulating agents. International Patent Publication WO 96/10586 discloses a method for preparing a fat substitute based on hydrolyzed granular starch. U.S. Pat. No. 5,919,486 discloses a powder preparation that comprises a porous starch grain carrier and a material carried within the pores of the carrier, the porous starch grain carrier having been prepared by partially hydrolyzing starch with raw starch digestive enzyme.

Other starches also have been used in dusting powder applications for many years, primarily to absorb more fluids from the skin. For example, U.S. Pat. No. 4,568,539 discloses compositions said to exhibit excellent moisture absorbency and comprising starch and a specific pregelatinized starch. Another document, EP 182,296, discloses a body dusting powder that comprises a porous starch granule which consists essentially of the residue remaining after about from 45% to 95% by weight of the granular starch has been solublized with an enzyme.

Skin fluids found on the skin surface typically comprise a complex mixture of sebum, lipids, sweat, and environmental or applied material. Because such fluids can provide nutrients and a moisture-rich environment for microorganism to proliferate, such fluids can cause body odors and even in some cases bacterial and fungal infections. These effects can be mitigated by applying a fluid-absorbing effective amount of a powdered starch composition as described in the prior art, or other known absorbents such as talc, cellulose derivatives, and so forth. The aforementioned starch-based compositions are said to control excess moisture, (i.e. the aqueous component of skin fluid), but are not said to control the oily secretions produced by sebaceous glands.

It is a general object of the invention to provide a method for preparing a fluid absorber that is effective in absorbing oil from the skin, and, more generally, that is effective in absorbing fluid from the skin. In other embodiments it is a general object to provide a fluid absorber.

THE INVENTION

It has now been discovered that in many cases the oil absorbency of a porous starch product will be maximized at a starch hydrolysis level that is less in the hydrolysis level at which water absorption is maximized. The invention makes use of this discovery by providing a method in which the hydrolysis level of the starch is controlled to optimize the fluid absorbency properties of the porous starch granules for use in absorbing fluid from the skin. It has further been found that oil absorption of a porous starch granule will reach a plateau after hydrolysis has proceeded to a certain extent, typically from about 30% to about 60%. The invention makes use of this discovery in certain embodiments to provide an essential fluid absorber not only for use in absorbing fluids from the skin, but also for use in numerous other applications, such as a carrier. The term "fluid absorber" thus may be deemed to include without limitation a product that in intended use absorbs fluid (such as from the skin) or a product that carries another product, i.e. a carrier.

In accordance with a preferred embodiment of the invention, a method is provided for preparing a fluid absorber. Generally, a granular starch and an enzyme for hydrolysis of the starch are selected, and, based on the starch and enzyme chosen, a fluid absorption optimum hydrolysis level is estimated. The starch then is enzymatically hydrolyzed under reaction conditions suitable to result in a porous granular starch, and the enzymatic hydrolysis is terminated when the hydrolysis has proceeded through a point within a predetermined range, typically within ±15%, or less, of the estimated fluid absorption optimum hydrolysis level. In other general embodiments, the starch is hydrolyzed without the use of an enzyme catalyst. In some embodiments, two hydrolyses are performed; one an acid hydrolysis that is not catalyzed enzymatically and one that is catalyzed enzymatically. These hydrolyses may be performed sequentially, in either order. In accordance with another embodiment of the invention, a method for absorbing fluid from the skin is provided. The method comprises applying a fluid-absorbing effective amount of porous starch granules prepared as described above. The fluid absorption optimum hydrolysis level may in some embodiments be considered to be that in which the oil absorption is maximized. In other embodiments of the invention, the fluid absorption optimum hydrolysis level may be based on the cumulative absorbence of the porous starch granule for various fluids, such as fluids that approximate the fluids found on the skin. One such fluid is a fluid that is composed of a mixture of water, 1% saline (NaCl), and oil. The invention further encompasses a fluid absorber prepared in accordance with the present teachings. Other features and embodiments of the invention are set forth hereinbelow.

DESCRIPTION OF PREFERRED EMBODIMENTS

Figure 1:
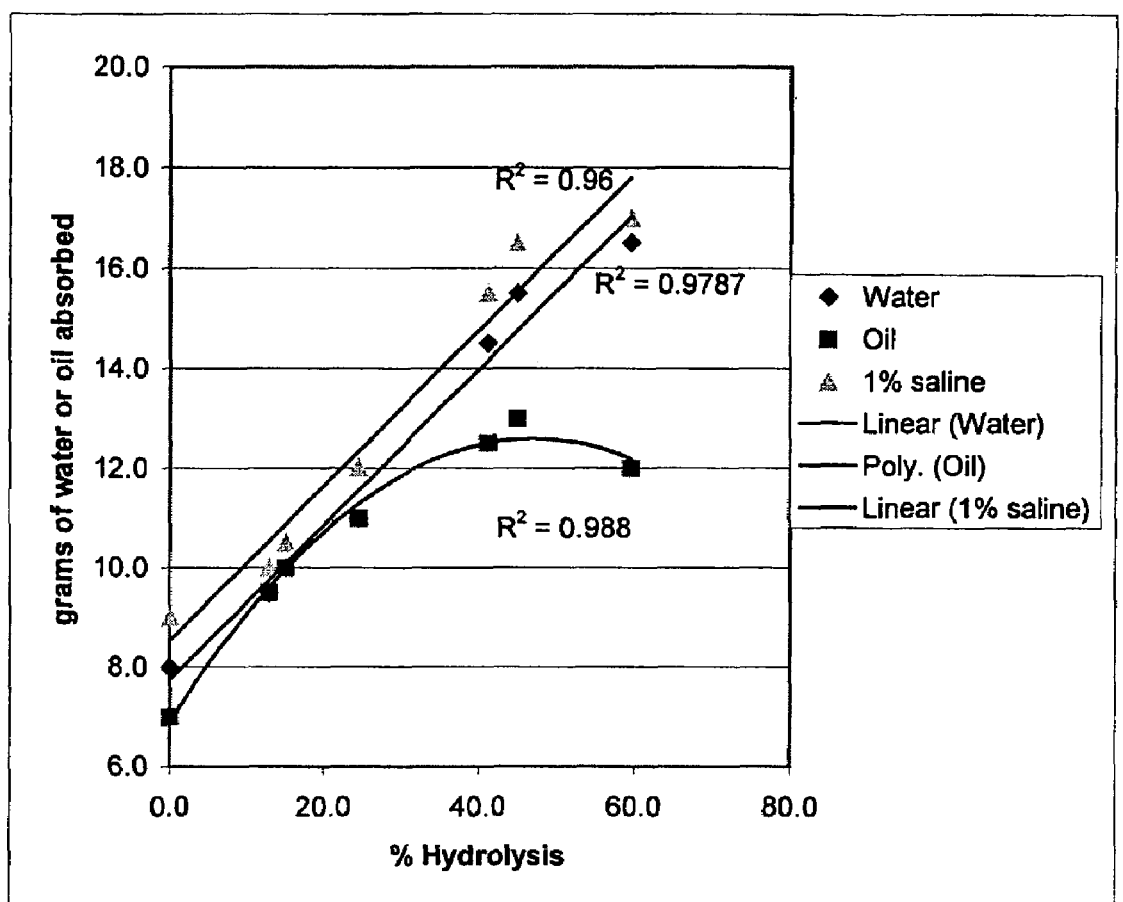
FIG. 1 is a graph illustrating the data set forth in Example 1.

Generally, the invention contemplates the partial hydrolysis of a granular starch, preferably with an enzyme. The starches that may be used as starting materials in preparing the porous starch granules may be derived from any native source, and typical starch sources include cereals, tubers, roots, legumes, and fruits. Exemplary starches include those obtained from corn, potato, wheat, rice, sago, tapioca, and sorghum. Corn starch is preferred in light of its low cost and ready availability, and also in light of the known skin affinity of corn starch and relative ease of modification of the granular structure of corn starch compared to starches such as potato. Suitable starches include pearl starches, such as PURE-DENT® B700 and corn starch B200, both sold by Grain Processing Corporation of Muscatine, Iowa. The starches used in conjunction with the invention not only may be native starches but also may be starches that have been modified prior to enzymatic hydrolysis. Exemplary of such modified starches are crossed-linked starches, which may comprise a native starch that have been crossed-linked via any suitable cross-linking technique known in the art or otherwise found to be suitable in conjunction with the invention. An example of a commercially available cross-linked starch is PURE-DENT® B850, sold by Grain Processing Corporation of Muscatine, Iowa. Other starches are deemed suitable for use in conjunction with the invention, and thus, it is contemplated that, for instance, derivatized, or acid-thinned starches, or starches that have otherwise modified may be employed. Exemplary starches include PURE-SET® B950, PURE-SET® B990, PURE-COAT® B70, SUPERBOND® B300, SUPERCORE® S22, COATMASTER® K56F and starch C-165, all available from Grain Processing Corporation, Muscatine, Iowa.

In accordance with the invention, the starch is partially hydrolyzed, preferably with an enzyme. Suitable enzymes for using in conjunction with the invention include any of the wide variety of art-recognized enzymes suitable for hydrolyzing starch, and include, for instance, amylases derived from fungal, bacterial, higher plant, or animal origin. Preferred examples of suitable enzymes include endo-alpha-amylases, which cleave the 1-4 glucoside linkage of starch. In addition, the enzyme may include or comprise a beta-amylase, which removes maltose-units in a stepwise fashion from the non-reducing ends of the alpha 1-4 linkages; a glucoamylase, which remove glucose units in a stepwise manner from the non-reducing end of starch and which cleaves both 1-4 and the 1-6 linkages; and debranching enzymes such as isoamylase and pullulanase which cleave the 1-6 glucosidic linkages of the starch. Such enzymes can be used alone or in combination. More generally, any starch that hydrolyses granular starch via the porous starch granules may be employed in conjunction with the invention.

Preferred sources of alpha-amylases and pullulanases include several species of the *Bacillus* micro-organism, such as *Bacillus subtilis, Bacillus licheniformis, Bacillus coagulans, Bacillus amyloliquefaciens, Bacillus stearothermophilus,* and *Bacillus acidopullulyticus*, preferably the thermal stable amylases produced by *Bacillus stearothermophilus, Bacillus licheniformis,* and *Bacillus acidopullulyticus*. Maltogenic alpha-amylase, an enzyme that produces high quantities of maltose and low molecular weight saccharides, is produced in *Bacillus* species; this enzyme can be obtained from Novo Nordisk under the trademark MALTOGENASE™. Preferred glucoamylases include those obtained from strains from *Aspergillus niger*. One alpha-amylase suitable in conjunction with the invention is G995, an alpha-amylase enzyme that is commercially available from Enzyme Biosystems LTD. One glucoamylase that is suitable for use in conjunction with the invention is G990, sold by Enzyme Biosystems Ltd.

The starch should be partially hydrolyzed with the selected enzyme to yield a porous starch granule. Generally, the enzymatic hydrolysis is accomplished in an aqueous or buffered slurry at any suitable starch solids level, preferably a solids level ranging from about 10% to about 55% by weight on dry starch basis, more preferably about 25% to about 35% by weight. The pH and temperature of the slurry should be adjusted to any conditions effective to allow enzyme hydrolysis. These will vary depending on the enzyme and starch selected, and are not critical so long as the starch does not gelatinize; generally, this can be accomplished so long as the temperature remains below the gelatinization temperature of the starch. In general, the pH will range from about 3.5 to about 7.5, more preferably from about 4.0 to about 6.0. To reach this pH, any suitable acid or base may be added, or a buffer may be employed. The temperature preferably is maintained at least 3° C. below the gelatinization temperature of the starch. For corn starch, the gelatinization temperature falls within a range between about 62° and 72° C. Accordingly, the temperature of the slurry should be below about 62° C., preferably ranging from about 22° C. to about 59° C., and more preferably from about 51° C. to about 61° C.

The enzyme may be employed in any amount suitable to effectuate a partial hydrolysis of the starch granules in the slurry. Preferably, the enzyme is employed in the slurry in a concentration ranging from about 0.2% to about 3% by weight on dry starch, and more preferably from about 0.4% to about 2%. For glucoamylase, this range is based on a 300 unit per ml enzyme (based on the Enzyme Biosystems unit definition); for alpha-amylase, this range is based on a 2200-5000 unit/ml enzyme For the maltogenic alpha-amylase, the units are based on a commercial 4000 unit/ml enzyme (MALTOGENASE from Novo Nordisk).

When it is desired to terminate the enzymatic hydrolysis, the enzymatic hydrolysis may be terminated by any suitable techniques known in the art, including acid or base deactivation, ion exchange, solvent extraction, or other suitable techniques. Preferably, heat deactivation is not employed, since a granular starch product is desired and since the application of heat in an amount sufficient to terminate the enzymatic reaction may cause gelatinization of the starch. For typical enzymes, acid deactivation may be accomplished by lowering the pH to a value lower than 2.0 for at least 5 minutes, typically for 5 to 30 minutes. After deactivation, the pH of the slurry may be readjusted to the desired pH according to the intended end use of the granules. Typically, the pH will be adjusted to a pH within the range from about 5.0 to 7.0, more preferably from about 5.0 to about 6.0. The starch granules thus prepared then can be recovered using techniques known in the art, including filtration and centrifugation. Preferably, the reducing sugars and other byproducts produced during the enzymatic treatment are removed during the washing steps. Most preferably, the starch granules subsequently are dried to a moisture content of or below about 12%.

In other embodiments of the invention, the starch granules are hydrolyzed via acid hydrolysis without the use of an enzyme. In such embodiments, the starch is placed in an aqueous acid medium at a low pH (typically a pH below 2.0, and more preferably below 1.0) at an elevated temperature for a time sufficient to hydrolyze the starch. Those skilled in the art will appreciate that many reaction conditions may be employed. For instance, the hydrolysis time may range from a few hours to a period of days. Generally, the starch solids level and temperature should be within the ranges described above with respect to enzymatic hydrolysis. When it is desired to terminate the hydrolysis, the pH should be adjusted to a level sufficient to terminate substantially completely the hydrolysis (typically to a pH ranging from about 5-7). The starch is preferably dried, as discussed hereinabove. While this method is suitable for the hydrolysis of starch, use of an enzyme is preferred, inasmuch as it is believed such use will provide a degree of regional specificity of hydrolysis of the starch granule that will be lacking absent the use of an enzyme. It is further believed that the use of an enzyme will affect the absorption properties of the resulting porous starch granules. Also, enzyme catalysts allow operation at more moderate pH levels.

In some embodiments of the invention, two hydrolyses are performed; one an emzymatically catalyzed hydrolysis and one not catalyzed enzymatically. The hydrolyses may be performed in either order. Preferably, the first of the hydrolyses is terminated after the starch granule has been hydrolyzed to an extent of about 50% of the desired extent of hydrolysis and the second hydrolysis is next commenced and allowed to proceed to finish the hydrolysis to the desired extent. More generally, the first hydrolysis may be allowed to proceed from about 10% to about 90% of the desired extent.

In accordance with a preferred embodiment of the invention, the starch is hydrolyzed to an optimum fluid absorption hydrolysis level. By "hydrolysis level" is contemplated the percentage of the starch granule that is enzymatically hydrolyzed and thus no longer remaining in granular form. The optimum fluid absorption hydrolysis level most preferably is determined empirically, that is, by testing the absorption properties for a specific starch hydrolyzed with the specific enzyme being contemplated at various hydrolysis levels and estimating from this information the hydrolysis level that yields the optimum fluid absorption property. The hydrolysis level alternatively may be determined via reference to a predetermined correlation of fluid absorption levels and hydrolysis levels. If the optimum hydrolysis level is known in advance, the "determination" of the optimum hydrolysis level may be simply predetermining the hydrolysis level with reference or regard to the known optimum level. In any event, the extent of hydrolysis of starch in a given hydrolysis reaction may be determined or estimated from the reaction time.

The optimum fluid absorption property may be defined in any manner consistent with the ultimate intended purpose of the starch, for instance, in connection with the goal of absorbing fluids from the skin. For instance, in one embodiment of the invention, the optimum fluid absorption may be defined as the maximum oil absorption, i.e., the fluid absorption optimum hydrolysis level may be taken as the minimum hydrolysis level at which oil absorption is maximized (reaches an apparent plateau). Any suitable oil, such as a mineral oil, may be used to approximate oils found in the surface of the skin. More generally, other fluids may be used to approximate the composition of fluids on the skin. For instance, the fluid on the surface of the skin may be estimated to comprise a combination of water, 1% saline (NaCl), and oil. The fluid absorption optimum hydrolysis level may be regarded as that hydrolysis level at which the absorption of oil water, 1% saline, and oil is deemed to be cumulatively optimized; this may be regarded as the minimum hydrolysis level at when the oil absorption reaches an apparent maximum. Alternatively, weighting factors may be applied to the water, saline, and oil absorption parameters in order to further approximate the composition of fluids from the skin. Such weighting factors may be empirically determined. If there is no one level which the fluid absorption is maximized (for instance, if there is a range of hydrolysis levels at which fluid hydrolysis is constant), any point in such range may be regarded as the optimum level. Alternatively, the lowest hydrolysis level in such range may be regarded as optimum. In other embodiments the optimum fluid hydrolysis level may be empirically estimated.

The enzymatic or acid hydrolysis should be allowed to continue to within a selected range surrounding the estimated fluid absorption optimum hydrolysis level. Any suitable range may be selected. For instance, once the fluid absorption optimum hydrolysis level has been estimated, the hydrolysis may be allowed to proceed to within ±15%, more preferably ±10% and even more preferably ±5%, of the estimated optimum level. For instance, using corn starch, the optimum hydrolysis level in several embodiments may range from about 30% to about 50%, in some embodiments, about 30% to about 44%; in other embodiments; from about 35% to about 44%; in other embodiments from about 38% to about 42%; and in other embodiments the hydrolysis level may be about 40%. This optimum represents the lowest hydrolysis level at which oil absorption reaches an apparent plateau.

Once the fluid absorption optimum hydrolysis level has been determined, the starch is hydrolyzed with the enzyme to within the selected range surrounding the optimum level. The granules can be recovered using any suitable technique known in the art or otherwise found to be suitable, including filtration and centrifugation.

In preparing a fluid absorber for the skin, the starch granules thus prepared most preferably are ground to provide ground granules after washing and drying. In absorbing fluid from the skin, the ground granules may be applied in any amount effective to absorb fluid therefrom. The ground granules may be used alone, or in combination with other ingredients. In accordance with one embodiment of the invention, for instance, a fluid absorber includes the ground granules prepared in accordance with the present technical and a fragrance. In other embodiments, the granules are used as a carrier for materials such as colorants, flavorants and other materials (in particular oleogenous materials).

Exemplary applications for the non-ground starches prepared in accordance with the invention include plating agents for flavors and fragrances; plating agents for sticky or oily food products such as peanut butter, honey, and molasses; plating of lecithin; plating of colors; flow aids on shredded cheeses; stabilizing agents for products (e.g. cream cheese, to keep oil from separating out); coating agents (e.g., for pepperoni slices to prevent sticking together); plating for fats, such as chicken fat; plating to prevent oil separation in sauces; flow aids in dry sauce mixes; absorbers for moisture in dry mixes; plating agents for pharmaceutically active materials (e.g. prior to encapsulation); plating of oleoresins; carriers for oils such as fish oil, and thickeners for materials such as oils (e.g. olive oil). Exemplary applications for the ground starches prepared in accordance with the invention include fluid absorbing agents in body and "shower" powders; fluid absorbing agents in other personal care products such as dry hair care products, lip balms, antiperspirants and deodorants, foot powers, dispensing body powders, natural soaps, sun tan lotions, and body lotions; plating agents for colors and flavors (for instance, as a carrier for colorants for facial powder); plating agents for pharmaceutically active materials; absorbents in medicated patches and plating agents for simethicone. This list is by no means exhaustive, but to the contrary it is contemplated that the starches prepared in accordance with the invention will find use in numerous other applications. More generally, any starch that has been hydrolyzed via enzymatic hydrolysis or otherwise to form a fluid absorber should be deemed useful in connection with such applications. The invention should be deemed to include the use of such porous starches in such applications. Preferably, but necessarily, the starch used in such applications is hydrolyzed to an estimated fluid absorption optimum hydrolysis level.

The following examples are provided to further illustrate the invention, but should not be construed as limiting the invention in scope.

EXAMPLES

The following procedure was used to estimate water, saline, and oil absorption.

Prior to testing, each sample was screened through a 120 mesh (US) screen (0.0125 cm-0.0049 in.). In accordance with ASTM D281-95, to 10.0 g (dry solid basis) starch (weighed in a 100 ml beaker) was added dropwise water, 1% salt water, or a mineral oil (CHEVRON SUPERLA #7) until a stiff, putty-like paste was formed. The precision of this test is +/−0.5 ml and gives an indication of the saturation value of the starch.

Example 1

This example shows how the degree of hydrolysis can affect the water, salt water, and oil absorption properties of starch granules.

In 1250 ml tap water was slurried 500 grams (dry solids basis) of dent corn starch. The slurry was heated to a temperature of either 51° C. or 60° C., as indicated in Table 1, and the pH was adjusted to the indicated value using dilute hydrochloric acid. The amount of alpha-amylase (G995, commercially available from Enzyme Bio-Systems Ltd., and BAN and TERMAMYL 120 L, commercially available from Novo Nordisk) indicated in Table 1 was added and the reaction was allowed to proceed at the indicated temperature with constant mixing for the indicated amount of time. The enzyme was then deactivated by reducing the pH to 1.9 with dilute hydrochloric acid. After 5 minutes at pH 1.9, the pH of the slurry was adjusted to 5.0-5.5 with dilute sodium hydroxide. The reaction mixture was filtered, washed with tap water, and dried. The hydrolysis conditions and absorption test results are shown in Table 1. "Yield" in these tables refers to yield of insoluble starch granules.

TABLE 1

| Conditions | | | | | Absorption (ml/10 g basis) | | |
|---|---|---|---|---|---|---|---|
| Temp. | pH | Enzyme | Time | Yield | Water | 1% Salt | Oil |
| — | — | None | — | — | 8.0 | 9.0 | 7.0 |
| 51° C. | 6.30 | 0.26 ml BAN | 8 h | 87.1% | 9.5 | 10.0 | 9.5 |
| 51° C. | 6.50 | 0.26 ml TERMAMYL | 8 h | 84.9% | 10.0 | 10.5 | 10.0 |
| 51° C. | 5.80 | 0.13 ml G995 | 24 h | 75.5% | 11.0 | 12.0 | 11.0 |
| 60° C. | 5.20 | 1.3 ml G995 | 8 h | 58.8% | 14.5 | 15.5 | 12.5 |
| 51° C. | 5.80 | 1.30 ml G995 | 48 h | 55.0% | 15.5 | 16.5 | 13.0 |
| 60° C. | 5.80 | 13.0 ml G995 | 8 h | 40.4% | 16.5 | 17.0 | 12.0 |

In this example, water and 1% salt water absorption of alpha-amylase treated corn starches are similar and increase with increasing hydrolysis yield, while a limit surprisingly is observed with oil absorption, this limit occurring at around 60% yield (40% hydrolysis). All alpha-amylase treated starches display higher water and oil absorption than untreated corn starch. FIG. 1 shows that, for water and 1% saline, the relationship between absorption and percent hydrolysis is essentially linear over a broad range, while the oil absorbance reaches a plateau.

Example 2

This example shows how the degree of hydrolysis can affect the water and oil absorption of starch granules that have been hydrolyzed with a maltogenic alpha-amylase, and how similar treatment with alpha-amylase or a maltogenic alpha-amylase can lead to different absorption properties.

500 grams (dry solids basis) of dent corn starch were slurried in 1250 ml tap water. The slurry was heated to 60° C. and the pH adjusted to 5.15 using dilute hydrochloric acid. The amount of maltogenic alpha-amylase (MALTOGENASE 4000L, commercially available from Novo Nordisk) indicated in Table 2 was added and the reaction was allowed to proceed at 60° C. with constant mixing for the indicated amount of time. The enzyme was then deactivated by reducing the pH to 1.9 with dilute hydrochloric acid. After 5 minutes at pH 1.9, the pH was adjusted to 5.0-5.5 with dilute sodium hydroxide. The reaction mixture was filtered, washed with tap water and dried. The hydrolysis conditions and absorption test results are shown in Table 2.

TABLE 2

| Conditions | | | | | Absorption (ml/10 g basis) | | |
|---|---|---|---|---|---|---|---|
| Temp. | pH | Enzyme | Time | Yield | Water | 1% Salt | Oil |
| — | — | None | — | — | 8.0 | 9.0 | 7.0 |
| 60° C. | 5.15 | 2.0 ml MALTOGENASE | 8 h | 85.7% | 11.0 | 11.0 | 8.5 |
| 60° C. | 5.15 | 5.0 ml MALTOGENASE | 8 h | 77.0% | 11.0 | 11.5 | 11.0 |
| 60° C. | 5.15 | 10.0 ml MALTOGENASE | 24 h | 69.8% | 13.5 | 12.5 | 11.0 |
| 60° C. | 5.15 | 10.0 ml MALTOGENASE +5.0 ml MALTOGENASE | 8 h +5 h | 54.7% | 14.5 | 15.0 | 11.0 |

In the last experiment, the starch was treated with 10 ml MALTOGENASE for 10 hours, and 5 ml MALTOGENASE were subsequently added and the reaction allowed to proceed for 5 hours. In this example, water and 1% salt water absorption of maltogenic alpha-amylase treated corn starches are similar and increase with increasing hydrolysis yield, while a limit is observed with oil absorption, occurring at around 70% yield. Oil absorption was lower for the of maltogenic alpha-amylase treated starches of the example than for the alpha-amylase treated starches of example 1. For a similar hydrolysis level, oil absorption of alpha-amylase and of maltogenic alpha-amylase treated starches were different.

Example 3

This example shows how the level of hydrolysis can affect the water and oil absorption of starch granules, and how similar treatment with different enzymes can lead to different absorption properties.

500 grams (dry solids basis) of dent corn starch were slurried in 1250 ml tap water. The slurry was heated to 60° C. and the pH adjusted to 5.20 using dilute hydrochloric acid. The amounts of alpha-amylase and pullulanase (G995 and ULTRADEX, a pullulanase enzyme commercially available from Enzyme Bio-Systems Ltd., PROMOZYME, a pullulanase enzyme commercially available from Novo Nordisk) indicated in Table 3 were added and the reaction was allowed to proceed at 60° C. with constant mixing for the indicated amount of time. The enzymes were then deactivated by reducing the pH to 1.9 with dilute hydrochloric acid. After 5 minutes at pH 1.9, the pH was adjusted to 5.0-5.5 with dilute sodium hydroxide. The reaction mixture was filtered, washed with tap water and dried. The hydrolysis conditions and absorption test results are shown in Table 3.

TABLE 3

| Conditions | | | Absorption (ml/10 g basis) | | |
|---|---|---|---|---|---|
| Enzyme | Time | Yield | Water | 1% Salt | Oil |
| None | — | — | 8.0 | 9.0 | 7.0 |
| 0.65 ml G995 + 2.6 ml PROMOZYME | 2 h | 71.2% | 12.5 | 12.5 | 10.5 |
| 1.3 ml G995 + 1.3 ml ULTRADEX | 6 h | 61.3% | 14.0 | 15.0 | 12.5 |
| 2.6 ml G995 + 2.6 ml ULTRADEX | 6 h | 56.1% | 15.0 | 14.5 | 12.0 |
| 4.0 ml G995 + 4.0 ml ULTRADEX | 8 h | 52.5% | 16.0 | 16.0 | 11.5 |

The water, and 1% salt water absorption of alpha-amylase-pullulanase treated corn starches of this example were similar to alpha-amylase treated starches of example 1, while a lower oil absorption limit was observed, occurring at around 60% hydrolysis yield.

Example 4

This example demonstrates that the degree of hydrolysis can affect the water and oil absorption of starch granules, and how similar treatment with different enzymes can lead to different absorption properties.

500 grams (dry solids basis) of dent corn starch were slurried in 1250 ml tap water. The slurry was heated to 60° C. and the pH adjusted to 5.20 using dilute hydrochloric acid. The amounts of glucoamylase and alpha-amylase (G990 and G995, commercially available from Enzyme Bio-Systems Ltd.) indicated in Table 4 were added and the reaction was allowed to proceed at 60° C. with constant mixing for the indicated amount of time. The enzymes were then deactivated by reducing the pH to 1.9 with dilute hydrochloric acid. After 5 minutes at pH 1.9, the pH was adjusted to 5.0-5.5 with dilute sodium hydroxide. The reaction mixture was filtered, washed with tap water and dried. The conditions and absorption test results are shown in Table 4.

TABLE 4

| Conditions | | | Absorption (ml/10 g basis) | | |
|---|---|---|---|---|---|
| Enzyme | Time | Yield | Water | 1% Salt | Oil |
| None | — | — | 8.0 | 9.0 | 7.0 |
| 5.0 ml G990 | 2 h | 91.8% | 11.5 | 11.0 | 8.5 |
| 5.0 ml G990 | 4 h | 90.5% | 12.0 | 11.5 | 8.5 |
| 10.0 ml G990 | 2 h | 89.7% | 12.5 | 12.5 | 8.5 |
| 5.0 ml G990 | 6 h | 87.5% | 12.5 | 12.5 | 9.0 |
| 10.0 ml G990 | 6 h | 70.4% | 14.0 | 14.0 | 9.0 |
| 0.05 ml G995 + 5.0 ml G990 | 8 h | 68.5% | 15.0 | 15.5 | 11.0 |
| 0.65 ml G995 + 5.0 ml G990 | 2 h | 50.9% | 16.5 | 16.5 | 11.5 |
| 1.3 ml G995 + 10.0 ml G990 | 2 h | 39.2% | 16.0 | 17.0 | 10.0 |
| 1.3 ml G995 + 10.0 ml G990 | 4 h | 28.3% | 17.5 | 17.5 | 10.5 |
| 1.3 ml G995 + 10.0 ml G990 | 6 h | 25.0% | 17.5 | 17.5 | 11.0 |
| 1.3 ml G995 + 10.0 ml G990 | 8 h | 21.0% | 18.5 | 18.0 | 10.5 |

Figure 2:
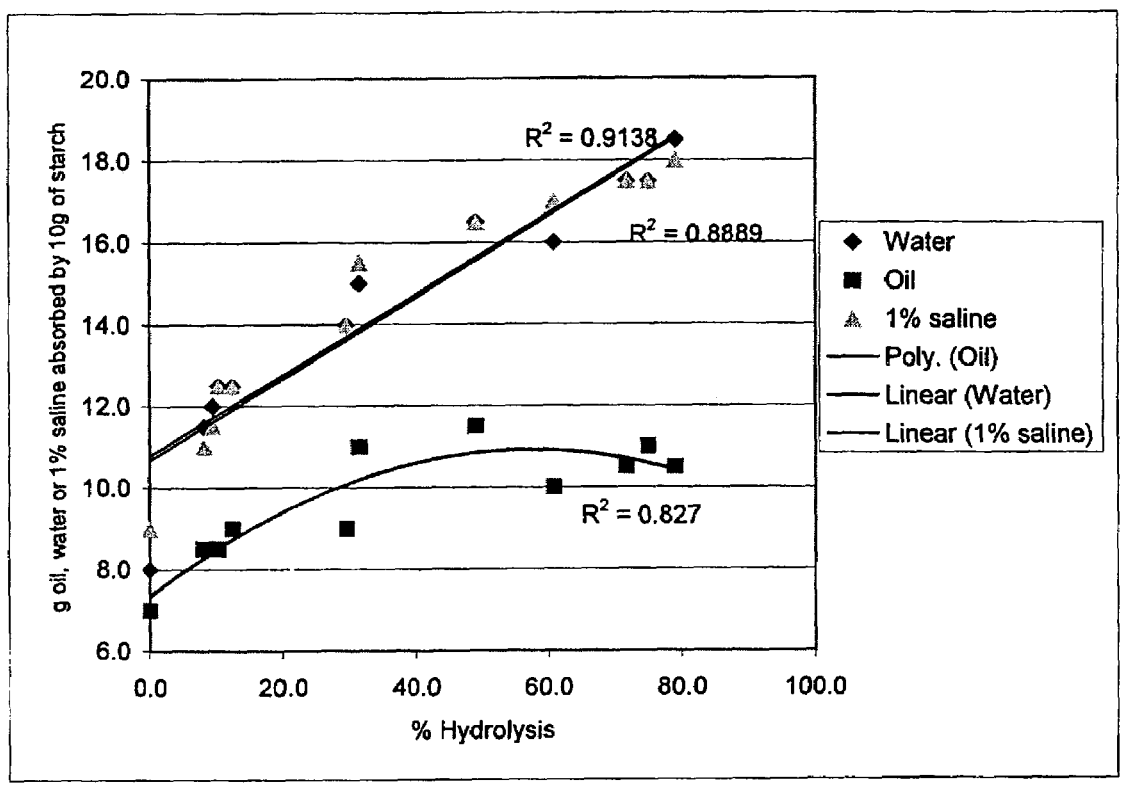
FIG. 2 is a graph illustrating the data set forth in Example 4.

FIG. 2 illustrates that the oil absorbance reaches a plateau at about 60% yield (40% hydrolysis), while absorbance of water and saline increases in an approximately linear manner.

Example 5

This example shows how the starch type can affect the water and oil absorption of starch granules, as indicated by hydrolysis level.

In separate experiments, 500 grams (dry solid basis) of B850, a highly cross-linked corn starch sold by Grain Processing Corporation of Muscatine, Iowa, and VINAMYL II, a high amylose starch sold by National Starch, & Chemical Company, were slurried in 1250 ml tap water. Each slurry was heated to 60° C. and the pH adjusted to 5.7 using dilute hydrochloric acid. The amounts of alpha-amylase (G995, commercially available from Enzyme Bio-Systems, Ltd.) indicated in Table 5 were added and the reaction was allowed to proceed at 60° C. with constant mixing for 8 h. The enzymes were then deactivated by reducing the pH to 1.9 with dilute hydrochloric acid. After 5 minutes at pH 1.9, the pH was adjusted to 5.0-5.5 with dilute sodium hydroxide. The reaction mixture was filtered, washed with tap water and dried. The hydrolysis conditions and absorption test results are shown in Table 5.

TABLE 5

| | G995 | % | Absorption (ml/10 g basis) | | |
|---|---|---|---|---|---|
| Starch Type | Dosage | Hydrolysis | Water | 1% Salt Water | Oil |
| Corn | — | — | 8.0 | 9.0 | 7.0 |
| Corn | 1.3 ml | 41.2 | 14.5 | 15.5 | 12.5 |
| B850 | — | — | 8.5 | 9.0 | 7.0 |
| B850 | 1.3 | 35.9 | 13.5 | 14.5 | 11.0 |
| B850 | 2.6 | 43.6 | 16.0 | 15.5 | 11.5 |
| High Amylose | — | — | 11.0 | 11.0 | 10.5 |
| High Amylose | 1.3 | 34.9 | 17.5 | 15.5 | 9.0 |

These results show that highly cross-linked corn starch and high amylose starch are not as susceptible to G995 hydrolysis than active corn starch, and that water and oil absorption can differ, for the same hydrolysis level, with the starch type. Water absorption in this example was the highest for high amylose starch while oil absorption was lower for this starch.

Example 6

This example shows how the alpha-amylase treated corn starch outperforms commercial baby powders for water, 1% salt water, and oil absorption.

TABLE 6

| | Absorption (ml/10 g basis) | | |
|---|---|---|---|
| Fluid Absorber | Water | 1% Salt Water | Oil |
| Commercial Talc | 7.0 | 8.0 | 8.5 |
| Commercial Talc | 8.0 | 9.0 | 10.5 |
| Commercial corn starch baby power | 10.0 | 9.5 | 7.5 |
| Alpha-amylase treated corn starch | 14.5 | 15.5 | 12.5 |

As seen, the starch of the present invention outperformed the commercial baby powders for water, 1% salt water, and oil absorption.

Example 7

This example demonstrates how the characteristics of granular starch can be affected by enzymatic treatment.

TABLE 7

| Starch | Enzyme Treatment | % Hydrolysis | Loose Bulk Density (g/cm$^3$) | Surface/Area (m$^2$/g) |
|---|---|---|---|---|
| Corn | — | — | 0.62 | 0.32 |
| Corn | α-Amylase G995 | 28.7 | 0.52 | 1.09 |
| Corn | α-Amylase G995 | 41.2 | 0.46 | 1.14 |
| Corn | G995/G990 | 75.0 | 0.49 | 1.34 |

As seen, the enzymatic treatment increases the surface area while lowering the density of the granules.

Example 8

This example illustrates the preparation of a fluid absorber via acid hydrolysis of starch.

Starch, (B200, 643.5 g dry solids basis) was added to 1250 mL of water to make a 34% solids slurry. The mixture was heated to 59° C. The pH was adjusted to below 1 by the addition of a total of 50 mL of 1:1 concentrated hydrochloric acid:water. After 24 hours at 59° C., the reaction was cooled and pH adjusted to 5.3 with soda ash. The resulting mixture was filtered, washed 2×400 mL with water and dried overnight at 50° C.

Example 9

This example illustrates the preparation of another fluid absorber.

A fluid absorber was produced according to the procedure described in Sample 8, except that 55 mL of 1:1 concentrated hydrochloric acid:water was used instead of 50 mL.

Example 10

This example illustrates the preparation of a fluid absorber via acid hydrolysis of starch followed by enzymatic hydrolysis.

Starch, (B200, 562 g dry solids basis) was added to 1250 mL of water to make a 40% solids slurry. The mixture was heated to 60° C. The pH was adjusted to below 1 by the addition of a total of 30 mL of 1:1 concentrated hydrochloric acid:water. After 17 hours at 60° C., the reaction was cooled and pH adjusted to 5.8 with soda ash. Enzyme (G995 α-amylase, 1.3 mL) was added to the mixture and it was stirred an additional 4 hours. The slurry was then cooled to room temperature. The pH of the reaction was then adjusted to 1.9 with 1:1 concentrated hydrochloric acid:water and held at this pH for five minutes to terminate all enzyme activity. The pH was then re-adjusted to 5.4 with 3% NaOH, and filtered, washed and dried as in Example 8.

Example 11

This example illustrates the preparation of another fluid absorber via acid hydrolysis of starch, followed by enzymatic hydrolysis.

Acid thinned starch (B950, 500 g dry solids) was added to 1250 mL of water to make a 28% solids starch slurry. The mixture was heated to 60° C. The pH was adjusted to 5.8 with 3% NaOH. Enzyme (G995 α-amylase, 1.3 mL) was added to the mixture and it was stirred for 4 hours. The slurry was then cooled to room temperature. The pH of the reaction was then adjusted to 1.9 with 1:1 concentrated hydrochloric acid:water and held at this pH for five minutes to terminate all enzyme activity. The pH was then re-adjusted to 5.4 with 3% NaOH, and filtered, washed and dried as in Example 8.

Example 12

This example illustrates the preparation of a fluid absorber by enzymatic hydrolysis of starch, followed by acid hydrolysis.

Starch, (B200, 500 g dry solids basis) was added to 1250 mL of water to make a 28% solids slurry. The mixture was heated to 60° C. The pH was adjusted to 5.8 with 3% NaOH. Enzyme (G995 α-amylase, 1.3 mL) was added to the mixture and it was stirred for 4 hours. The pH of the reaction was then dropped to below 1 by the addition of 50 mL of 1:1 concentrated hydrochloric acid:water. After 4 hours at 60° C., the reaction was cooled and pH adjusted to 5.8 with soda ash. The slurry was then filtered, washed and dried as in Example 8.

Example 13

This example illustrates the preparation of a second fluid absorber by enzymatic hydrolysis of starch followed by acid hydrolysis.

A fluid absorber was produced according to the procedure described in Example 12, except that 30 mL of 1:1 concentrated hydrochloric acid:water was used instead of 50 mL.

Example 14

Starch (B200, 500 g dry solids basis) was added to 1250 mL of water to make a 28% solids slurry. The mixture was heated to 60° C. The pH was adjusted to 5.8 with 1:1 concentrated hydrochloric acid:water. Enzyme (G995 α-amylase, 1.3 mL) was added to the mixture and it was stirred for 8 hours. The pH of the reaction was then adjusted to 1.8 with 1:1 concentrated hydrochloric acid:water and held at this pH for five minutes to kill enzyme activity. The pH was then re-adjusted to 5.3 with 3% NaOH. The mixture then was filtered, washed (2×400 mL) and dried. The resulting product had a oil absorbency of 12.0 mL per 10 g of starch and a water absorbency of 15.5 mL per 10 g of starch.

The following table summarizes absorption data for hydrolyzed granular starches made via enzyme, acid or combined enzyme/acid procedures outlined in examples 5 and 8 through 14.

| Sample | Treatment | % Yield | Absorption (mL/10 g) Water | Oil |
|---|---|---|---|---|
| B200 | None | — | 8.5 | 7.5 |
| Example 5 (entry 2 in Table 5) | Enzyme | 59 | 14.5 | 12.5 |
| Example 8 | Acid | 70 | 15 | 7.5 |
| Example 9 | Acid | 70 | 12.8 | 9.0 |
| Example 10 | Acid, then enzyme | 52 | 19.8 | 8.0 |
| Example 11 | Acid, then enzyme | 66 | 12.8 | 9.0 |
| Example 12 | Enzyme, then acid | 60 | 12.4 | 9.5 |
| Example 13 | Enzyme, then acid | 60 | 12.4 | 10.5 |
| Example 14 | Enzyme | 54 | 15.5 | 12.0 |

The data shows that acid hydrolysis and/or acid/enzyme hydrolysis do improve water and oil absorption when compared to untreated starch. Acid and enzyme sequential hydrolyses do not show any improvements over enzyme catalyzed acid hydrolysis, especially in the ability to absorb water and oil in relatively equal amounts. Acid hydrolysis, followed by enzyme hydrolysis may be a way to allow the enzyme more access to the granule, which could lead to some unique properties, as demonstrated by the high water absorption in Example 10. However, oil absorption of this sample was relatively low.

Example 15

This example illustrates the hydrolysis of starch to prepare a fluid absorber.

Based on the preceeding examples, it was determined that, for dent corn starch, the optimum hydrolysis level is about 40% ("optimum" being defined as the minimum hydrolysis level at which the oil absorption reaches an apparent plateau).

Dent corn starch slurry was diluted to 28% solids (Baume 15.8@ 60° F.). The total volume of the mixture was 380 gallons (1000 lbs). The pH of the mixture was adjusted to 5.6 by the addition of 250 mL of concentrated hydrochloric acid. The reaction temperature was adjusted to 136-140° F. and 1000 mL of G995 alpha amylase enzyme (Enzyme Biosystems) was added to the mixture. The reaction was stirred at temperature for 4 hours and then another 100 mL of G995 was added. The reaction was stirred for eight more hours. The pH of the reaction throughout the twelve-hour reaction time was held at 5.4-5.8. The reaction was then quenched by the addition of 2.0 L of concentrated HCL. The pH after quench was 1.9. The starch slurry was held at pH 1.9 for 15 minutes and then neutralized with 25.8 L of 3% NaOH to a pH of 5.3. The mixture was then filtered, washed and dried. The oil absorbance of 10 g of material was 13.0 mL.

Example 16

This example illustrates the preparation of a bleached product.

Dent corn starch was diluted to 28% solids (Baume 15.8@ 60° F.). The total volume was the mixture was 38 gallons (100 lbs). The pH of the mixture was adjusted to 5.6 by the addition of 18 mL of concentrated hydrochloric acid. The reaction temperature was adjusted to 136-140° F. and 100 mL of G995 alpha amylase enzyme (Enzyme Biosystems) was added to the mixture. The reaction was stirred at temperature for 4 hours and then another 100 mL of G995 was added. The reaction was stirred for eight more hours. The pH of the reaction throughout the twelve-hour reaction time was held at 5.4-5.8. The reaction was then quenched by the addition of 0.34 gallons of sodium hypochlorite (0.5%, 17.65% active chlorine). The hypochlorite addition was over a 20 minute period, and the final pH of the reaction was 8.2. One hour after the hypochlorite addition, sodium bisulfite, 100 grams, was added and the mixture was stirred for an additional fifteen minutes to ensure no residual oxidant remained. The pH of the mixture was then adjusted to 5.4, filtered and washed. The resulting product was dried and ground. The screen size of the ground product was 99.9% through a 100 mesh and 78% through a 325 mesh screen. The Minolta color of the sample was L=97.00, b=2.37. The water and oil absorbance of 10 g of material was 14.0 mL and 12.0 mL, respectively.

Example 17

The fluid absorber prepared in accordance with Example 15 is blended with a fragrance. The product thus prepared is used to absorb oil from the skin.

Example 18

The fluid absorber used in accordance with Example 15 is used to absorb an oleogenous flavoring agent. The product thus prepared is added to a food product to provide flavor.

It is thus seen that the invention provides a method for absorbing fluid from the skin, and also a method for preparing a fluid absorber.

While particular embodiments of the invention have been shown, it will be understood that the invention is not limited thereto since modifications may be made by those skilled in the art, particularly in light of the foregoing teachings. For instance, the invention is operable to absorb fluids not only from human skin but also from animal skin. It is, therefore, contemplated by the appended claims to cover any such modifications as incorporate those features which constitute the essential features of these improvements within the true spirit and scope of the invention. All references cited herein are hereby incorporated by reference in their entireties.

What is claimed is:

1. A method for preparing a fluid absorber, comprising:
   providing a granular starch;
   determining an estimated oil absorption maximum hydrolysis level for said starch;
   partially enzymatically hydrolyzing said starch under hydrolysis conditions suitable to provide a porous starch granule; and
   terminating said enzymatic hydrolysis when said starch has been hydrolyzed to an optimum oil absorption hydrolysis level ranging from about 30% to about 42%.

2. A method according to claim 1, said starch enzyme being selected from the group consisting of glucoamylase enzymes, alpha-amylase enzymes, maltogenic alpha-amylase enzymes, isoamylase enzymes, and pullulanase enzymes.

3. A method according to claim 1, said hydrolysis level ranging from about 35 to about 42%.

4. A method according to claim 1, said hydrolysis level ranging from about 38% to about 42%.

5. A method according to claim 1, said hydrolysis level being about 40%.

6. A method according to claim 1, including grinding said porous starch granules to form ground granules.

7. A method according to claim 1, said starch comprising corn starch.

8. A method according to claim 1, including adding a fragrance.

* * * * *